United States Patent [19]

Hesse

[11] Patent Number: 4,470,981
[45] Date of Patent: Sep. 11, 1984

[54] CHEMICAL COMPOUNDS

[76] Inventor: Robert H. Hesse, 49 Amherst St., Cambridge, Mass. 02142

[21] Appl. No.: 451,252

[22] Filed: Dec. 20, 1982

[51] Int. Cl.$^3$ ............................................. A61K 31/56
[52] U.S. Cl. ................................ 424/238; 260/397.2; 260/397.5
[58] Field of Search ......................... 260/397.5, 397.2; 424/238

[56] References Cited

U.S. PATENT DOCUMENTS 4,215,045  7/1980  Knapp, Jr. ........................ 260/397.2

Primary Examiner—Elbert L. Roberts
Attorney, Agent, or Firm—Bacon & Thomas

[57] ABSTRACT

The invention provides a compound of formula I

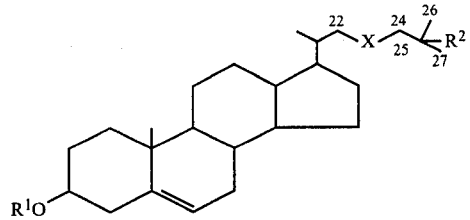

where $R^1$ represents hydrogen, lower alkanoyl or aryol, or tri-lower alkyl silyl, or a group $R^3$ —O—CO— (where $R^3$ represents lower alkyl); $R^2$ represents hydrogen, hydroxyl or fluorine and X represents —S—, —SO—, —SO$_2$—, —O—or —NR$^4$— (where $R^4$ represents hydrogen, lower alkyl or lower alkanoyl); the compounds are useful in the prophylaxis or management of cardiovascular disease through the regulation of serum cholesterol and a particularly useful compound is 23-thia-25-hydroxy-cholesterol.

8 Claims, No Drawings

CHEMICAL COMPOUNDS

This invention concerns novel compounds useful for reducing the level of serum cholesterol.

BACKGROUND OF THE INVENTION

One of the factors most clearly associated with the risk of cardio vascular disease is an elevated level of serum cholesterol particularly when associated with an inappropriate ratio of low density to high density lipoprotein. Intervention to reduce serum cholesterol levels is generally considered prudent medical practice. Unfortunately endogenous production of cholesterol is both considerable and stubbornly regulated and thus even severe dietary restriction has at best a limited effect. There has been therefore a considerable search for agents which suppress or limit endogenous production of cholesterol. One of the first of these discovered was triparinol which proved to be quite toxic and moreover blocked the biosynthesis of cholesterol at a rather late stage leading to accumulation of other sterol intermediates. These intermediates proved to be as unwelcome as cholesterol itself. It will be appreciated that there are many stages in conversion of acetate into cholesterol or precursor sterols, but it is well known that biochemical regulation of endogenous cholesterol synthesis is accomplished through a rather long feedback loop in which the product, cholesterol, inhibits further synthesis at the stage of the conversion of hydroxymethyl glutarate into mevalonate. Pharmacological intervention at this stage would therefore seem quite appropriate. It is now well known that 25 hydroxy cholesterol is a much more potent inhibitor of mevalonate synthesis than cholesterol itself, but large doses are still required for a pharmacological effect with unacceptable toxic side effects. Other exogenous agents which block the synthesis of mevalonate and thus cholesterol, notably the natural product compactin, have been found but in all cases the effect is either rather small or associated with toxicity.

DESCRIPTION OF THE INVENTION

Many derivatives of steroids and sterols have been prepared (and evaluated for various types of biological activity in which hetero atoms (most frequently oxygen or nitrogen) have replaced certain carbon atoms of the parent molecule. With the possible exception of testolactone such modifications have either greatly weakened or virtually eliminated biological activity. We have found surprisingly that replacement by a hetero atom of one of the side chain carbons (carbon 23) of certain sterols leads to new compounds which are extremely potent inhibitors of mevalonate biosynthesis.

These compounds are relatively free from toxic side effects and thus are useful agents in the prophylaxis or management of cardio vascular disease through the regulation of serum cholesterol. The new compounds are of the general formula I

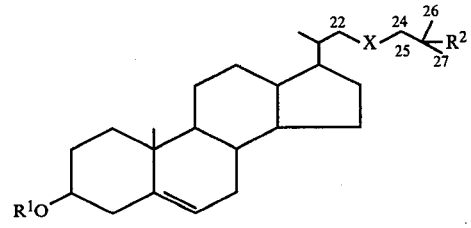

where $R^1$ represents hydrogen, lower alkanoyl or aryol, or tri-lower alkyl silyl, or a group $R^3$ —O—CO— (where $R^3$ represents lower alkyl); $R^2$ represents hydrogen, hydroxyl or fluorine (in general those compounds where $R^2$ represents hydroxyl or fluorine are more potent and thus preferred) and X represents —S—, —SO—, —SO$_2$—, —O— or —NR$^4$— (where $R^4$ represents hydrogen, lower alkyl or lower alkanoyl).

Particularly preferred compounds are those in which X represents —S—, —SO— or —SO$_2$—, particularly when $R^2$ represents hydrogen or hydroxyl; the compounds in which X represents —S— are most preferred, particularly the compound in which $R^2$ is hydroxyl. $R^1$ is preferably hydrogen or methyl. $R^2$ is advantageously acetyl.

The compounds of the invention may be prepared by various methods.

According to one method, a compound of the general formula II or III

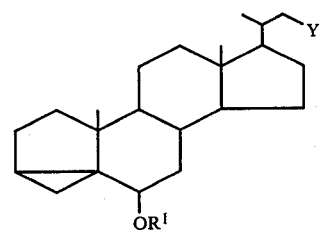

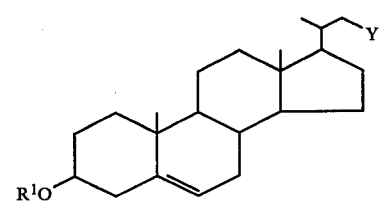

(in which $R^{1A}$ has the meaning given above for $R^1$ and Y represents a leaving group, for example a halogen atom, preferably iodine or bromine or an alkyl (preferably $C_{1-5}$) sulphonyloxy or aryl (preferably $C_{6-10}$ aryl) sulphonyloxy group, e.g. mesyloxy or tosyloxy) is reacted with a nucleophile HX; $CH_2$—$C(CH_3)_2$—$R^{24}$ (where X has the above meaning and $R^{24}$ has the meaning given for $R^2$ or is a protected hydroxyl group), or a nucleophilic derivative thereof, to give a compound of the formula IV

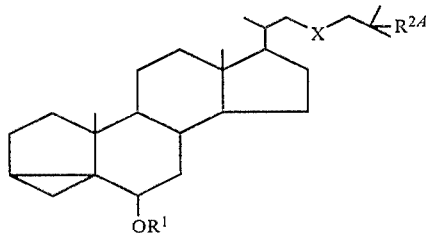

(from a compound of formula II) or a compound of formula I (from a compound of formula III) followed by treatment of the product of formula IV with acid in the presence of a nucleophile $R^1OH$, before or after optional oxidation of X from —S— to —S— or —$SO_2$— to give the desired product of formula I. The reaction is preferably carried out in the presence of a base, for example a hydride base. Where subsequent acidification is effected in aqueous acid, e.g. a sulphonic acid in an aqueous organic solvent, or compound I in which $R^1$=H is formed. Where anhydrous alkanoic acid is used, $R^1$ will be alkanoyl. Where anhydrous alkanol is present, $R^1$ will be alkyl.

Where $R^{24}$ is a protected hydroxyl group, this may, for example, be $C_{2-5}$ alkanoyl group such as acetyl, a $C_{2-5}$ alkoxycarbonyl or tri-$C_{1-5}$ alkyl silyl group.

According to a further method, a compound of formula II or III in which $R^{14}$ has the above meanings and Y represents OH, —SH or —$NHR^4$ may be reacted with a reagent of the formula

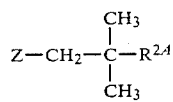

(in which $R^{24}$ has the above meaning and Z is a leaving group, for example a halogen atom, preferably iodine or bromine, or an alkyl or aryl sulphonyloxy group; or $R^{24}$ and Z together present an epoxide grouping), to give a compound of formula IV as defined above (from a compound of formula II) or a compound of formula I (from a compound of formula III), followed by acidification of a compound of formula IV as described above.

The reaction is preferably carried out in a polar non-protic solvent such as tetrahydrofuran, acetonitrile, dimethylformamide or hexamethylphosphoramide. A strong base is preferably present, for example a hydride such as sodium or potassium hydride or a tertiary alkoxide such as potassium t-butoxide, advantageously in the presence of a crown ether.

Compounds of the formula II or III in which X represents SH or $NHR_4$ may themselves be prepared from compounds of formula II or III where Y is a good leaving group as defined above through methods known to the art, for example treatment with $H_2S$ or an alkali metal xanthate followed by basic hydrolysis or through the Gabriel synthesis. In the first of the above methods is preferred where X will be —S— or —$NR^4$— and the second where X will be —O—.

Compounds of formula I or IV where X=—SO— are prepared from those where X=—S— through methods known to the art i.e. treatment with mild oxidants such as sodium meta periodate or prerbenzoic acid. Compounds of formula I or IV where X=$SO_2$— are prepared from those with X —S— or —SO— through methods known to the art, i.e. heating with per acid or through electrochemical oxidation etc. Finally compounds of formula I wherein $R^2$=OH may be prepared from those of formula I where $R^{24}$ is a protected hydroxyl group through methods known to the art i.e. treatment with NaOH or $Na_2CO_3$ in methanol where $R^{24}$ lower alkanoyloxy or lower alkoxycarbonyloxy or with tetrabutyl ammonium fluoride or acetic acid in tetrahydrofuran where $R^{24}$ is trialkyl silyloxy.

The compounds of formula II or III are easily prepared from plant sterols such as stigmasterol or phytosterols such as ergosterol. These preparations involve well known substances of formula II or III where X=OH for instance—see Helv. Chim. Acta. 57, 764 (1974).

In general the compounds of formula I of the present invention may be administered orally or parenterally at a dose range of 0.02 to 20 mg/kg preferably from 0.2 to 10 mg/kg. Usually a moderately low dose will be initially chosen and the dose then gradually adjusted to achieve the desired reduction of serum cholesterol. Tablets for oral administration comprise an effective dose of compound, together with standard excipients such as lactose, corn starch, calcium carbonate—with binders such as avicel, carboxyl methyl cellulose etc. and lubricants such as magnesium sterate etc. Capsules may contain solid excipients as above or an oily vehicle such as sesame, corn, or arachis oil. Parenteral compositions contain an effective dose of compound 1 together with an aqueous vehicle, a suspending agent such as carboxy methyl cellulose, Tween etc. and a preservative such as methyl or propyl paraben. The following examples are provided by way of illustration only:

EXAMPLE 1

1-mercapto-2-methyl-2-hydroxy-propane

Ethyl-2-mercapto acetate (10 ml) was added to dry ether (150 ml). The well-stirred solution was cooled to 0° C., and an ethereal solution of methyl magnesium bromide (3M soln, 100 ml, 3.3 eq) was added drop-wise over 1.5 hr. The mixture was removed from the ice bath and stirred for an additional 30 min. Ammonium chloride (18 g) in water was carefully added, and the mixture neutralised with hydrochloric acid to form 2 clear layers. The layers were separated and the ether layer washed with water/brine and dried. The solvent was removed under reduced pressure and the product distilled to give 4.4 g of the thiol b.p. 46° C./16 mmHg (lit. 64°/26 mm, 61°/22 mm); $^1$Hmmr 2.6 (d, J 9 Hz, C-1$H_2$); mass spec. m/e 59 (100), 73 (24), 91 (14).

EXAMPLE 2

1-amino-2-methyl-2-hydroxy-propane (2)

To a well-stirred mixture of lithium aluminium hydride (12 g) in ether (200 ml) at 0° C. was added dropwise over 1 hr a solution of acetone cyanohydrin (11.2 g, 12 ml) in ether (50 ml). The mixture was stirred at room temperature overnight. After cooling to 0° C., water (24 ml) was cautiously added dropwise. After the quenching was complete, anhydrous $Na_2SO_4$ (65 g) was added and stirring at room temperature was continued for a further 2.5 hr. The solid was filtered off and the ether evaporated to give, after distillation, 4.8 g (41%) of a viscous, colourless liquid. b.p. 74°–76° C./14 mm Hg (lit. 62°–64° C./13 mm Hg)$n_D^{20}$ 1.4463 (lit. $n_D^{20}$ 1.4467); $^1$Hmmr 2.6 (s. 2H), 1.87 (s, 3H, exchanges with $D_2O$), 1.2 (s, 6H); 1R max (thin film) 3400 (s), 3000 (m), 1600 (m), 1475 (m), 1380 (m), 1360 (m), 1220 (m), 1170 (m), 1110 (m), 960 (m), Cm$^{-1}$.

EXAMPLE 3

20 hydroxymethyl-6-$\beta$ methoxy-3$\alpha$, 5-cyclo-5$\alpha$-pregnane (3) and 20 tosyloxy-methyl-6-methoxy-3$\alpha$, 5-cyclo-5$\alpha$ pregnane (4) were prepared according to Uskokovic, Helv Chim Acta, 57, 764 (1974).

EXAMPLE 4

23-thia-25-hydroxy-6$\beta$-methoxy-3$\alpha$,5-cyclo-5$\alpha$-cholestane (5)

The tosylate (4) (2.25 g) in THF (100 ml) containing HMPTA (3 ml) and 1-mercapto-2-methylpropan-2-ol (2 ml) was degassed. NaH (50% disp. in oil, 800 mg) was added. After 3.5 hrs at room temperature, water was added, the mixture worked-up to give 1.4 g (72%) of the thia analogue (5). Crystalline from methanol. m.p. 97°–98° C.; $(\alpha)_D$ 72° (c 0.83); $^1$Hmmr 3.33 (s, C-6, OCH$_3$), 2.73 (m, W 7 Hz, C-6H), 2.63 (s, C-24H$_2$), 1.26 (s, C-26H$_3$), 1.03 (s, C-19H$_3$), 0.73 (s, C-18H$_3$); IR max 3600 (s), 2950 (s), 2900 (sh), 1475 (m), 1380 (m), 1170 (m), 1100 (m), 1090 (m), cm$^{-1}$; mass spec. molecular ion m/e 434; (analysis found: % C, 74, 73; H, 10.77; S, 7.57; $C_{27}H_{46}O_2S$ requires: % C, 74.60; H, 10.67; S, 7.38).

Similarly treatment of 4 with 2-fluoro-1-mercapto-2-methyl-propane (which can be prepared for instance by treatment of 1 with HF/pyridine complex or diethylaminosulfur trifluoride) gives the corresponding 23-thia-25 fluoro cyclo-cholesterol (6). Treatment of 1 with 2 in the absence of solvent gives 23-aza-25 hydroxycyclocholesterol (7), which on treatment with acetic anhydride and methanol gives 23-aza-23-acetyl-25-hydroxyhydroxy-cyclocholesterol (8). Tretment of 4 with iso butyl mercaptan gives the 23-thia 25-hydrogen compound (10).

EXAMPLE 5

23-thia-25-hydroxy-cholesterol 9

The i-steroid (5) (1.25 g) in dioxane (36 ml) and water (12 ml) containing p-toluenesulphonic acid (60 mg) was stirred at 80°–85° C. for 1.5 hr. After cooling to room temperature the mixture was diluted with CH$_2$Cl$_2$. Aqueous work-up gave 0.94 g (78%) of the cholesterol compound (9). Crystalline from methanol. m.p. 184°–185° C.; $(\alpha)_D$ 5.5° (c 0.545); $^1$Hnmr (30% DMSO d$_6$/CDCl$_3$; vol/vol; D$_2$O) 5.33 (m, W 8 Hz, C-6H), 3.4 (m, W 16 Hz, C-3H), 2.62 (s, C-24H$_2$), 1.27 (s, C-26H$_3$, C-27H$_3$), 1.15 (d, J 6Hz, C-21H$_3$), 1.0 (s, C-19H$_3$), 0.75 (s, C-18H$_3$); IR max 3550 (s), 2950 (s), 1640 (w), 1470 (m), 1440 (m), 1380 (m), 1135 (m), 1060 (m), cm$^{-1}$; mass spec. molecular ion m/e 420; (analysis found: %C, 74.15; H, 10.57; S, 7.62; $C_{26}H_{44}O_2S$ requires: %C, 74.23; H, 10.54; S, 7.62).

Similarly 6 gives 23-thia-25-fluoro-cholesterol (11), 7 gives 23-aza-25-hydroxy-cholesterol (12) and 8 gives 23-aza-23-acetyl-25-hydroxy cholesterol (13) and 10 gives 23-thia-cholesterol (14). Treatment of any of these compounds with one equivalent of acetic anhydride in pyridine affords the 3 monoacetate.

EXAMPLE 6

23-oxa-25-hydroxy-cholesterol (15)

A solution of 20-hydroxy-methyl-3-t-butyl-dimethyl-silyloxy-preg-5-ene (425 mg) in benzene (5 ml) containig dibenzo-18-crown-6 (100 mg), potassium-t-butoxide (500 mg) and isobutyene oxide (1 ml) is heated with reflux under argon until the starting material is consumed. The organic phase is washed successively with aqueous K$_3$PO$_4$H$_2$O, Aq. NaHCO$_3$ and brine, then evaporated to afford the title compound as the 3-t-butyl-dimethyl silyl ether. Treatment with H$_2$O/acetic acid/tetrahydrofuran—followed by removal of solvent and trituration with hexane affords the title compound.

EXAMPLE 7

100 tablets containing 50 mg of 23-thia-25-hydroxy-cholesterol are produced from the following ingredients: cpd 5, 50 gm, Lactose, 50 gm; Avicel 150 gm; cornstarch, 75 gm; Magnesium sterate, 5 gm. The active ingredient, lactose and avicel are mixed, blended with the cornstarch and magnesium sterate, and then pressed into 1000, 430 mg tablets, each containing 50 mg of active ingredient.

EXAMPLE 8

The following assay was performed.

Aortic smooth muscle cells were incubated for 24 hrs. at 37° C. in the presence of various inhibitors. Cells were then harvested, homogenized and assayed for the ability to convert $^{14}$C hydroxymethylglutaryl CoA into $^{14}$C mevalonate. The cytotoxic effect of inhibitors was evaluated by observation of morphological changes in the cells following the incubation period.

| Inhibitor | n/mole mevalonate hr/mg protein | Appearance |
|---|---|---|
| control | 2.75 | normal |
| vehicle | 2.59 | normal |
| 250 H cholesterol 2.5 μg/ml | 1.01 | moderate rounding |
| 250 H cholesterol 10 μg/ml | 0.69 | severe rounding |
| 23-thia-25-hydroxy cholesterol (9) 1 μg/ml | 0.1 | normal |
| 23-thia-25-hydroxy cholesterol (9) 10 mg/ml | 0.1 | slight rounding |

Triparinol and compactin each cause moderate to severe rounding of cells at doses which inhibit mevalonate production.

What is claimed is:

1. A compound of formula I

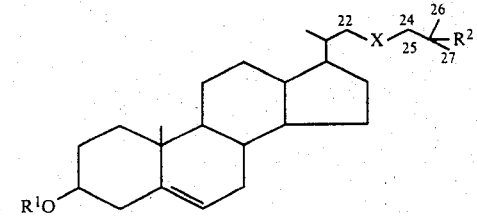

where R$^1$ represents hydrogen, lower alkanoyl or aryol, or tri-lower alkyl silyl, or a group R$^3$ —O—CO— (where R$^3$ represents lower alkyl); R$^2$ represents hydrogen, hydroxyl or fluorine and X represents —S—; —SO—, —SO$_2$—, —O— or —NR$^4$— (where R$^4$ represents hydrogen, lower alkyl or lower alkanoyl).

2. A compound as claimed in claim 1 wherein X is either —S—, or —SO— or —SO$_2$—.

3. A compound as claimed in claim 1 wherein X is either —S—, or —SO—, or —SO$_2$— and R$_2$ is either hydrogen or hydroxyl.

4. A compound as claimed in claim 1 wherein X is —S—.

5. A compound as claimed in claim 1 wherein X is —S— and $R^2$ is hydroxyl.

6. A composition comprising a compound of claim 1 in sufficient amount to lower serum cholesterol together with one or more inert and acceptable pharmaceutical excipients.

7. A method of lowering serum cholesterol comprising administration of a compound of claim 1 in an amount sufficient to accomplish said reduction together with any pharmaceutically acceptable vehicle or excipient.

8. A method for lowering serum cholesterol comprising administration of a compound of claim 1 at a dose of 0.02 to 20 mg/kg. together with a pharmaceutically acceptable vehicle or excipient.

* * * * *